US007238862B2

(12) United States Patent
Allison et al.

(10) Patent No.: US 7,238,862 B2
(45) Date of Patent: Jul. 3, 2007

(54) **EFFICIENCY *AGROBACTERIUM*-MEDIATED WHEAT TRANSFORMATION METHOD**

(75) Inventors: Helen Allison, Newmarket (GB);
Xiaorong Feng, Wildwood, MO (US);
Joyce E. Fry, St. Louis, MO (US);
Tianci Hu, Wildwood, MO (US);
Fengming Lu, Chesterfield, MO (US);
Maxim Radionenko, West Lafayette, IN (US)

(73) Assignee: Monsanto Technology LLC, St. Louis, MO (US)

( * ) Notice: Subject to any disclaimer, the term of this patent is extended or adjusted under 35 U.S.C. 154(b) by 876 days.

(21) Appl. No.: 10/064,849

(22) Filed: Aug. 22, 2002

(65) Prior Publication Data

US 2003/0154517 A1  Aug. 14, 2003

Related U.S. Application Data

(60) Provisional application No. 60/314,087, filed on Aug. 22, 2001.

(51) Int. Cl.
*C12N 15/84* (2006.01)
*A01H 4/00* (2006.01)

(52) U.S. Cl. ............... 800/294; 800/278; 800/320.1; 800/320.2; 800/320.3; 800/320; 435/469; 435/430.1; 435/431

(58) Field of Classification Search .................. None
See application file for complete search history.

(56) References Cited

U.S. PATENT DOCUMENTS 5,591,616 A  1/1997  Hiei et al. ............... 435/469

FOREIGN PATENT DOCUMENTS

| WO | WO 97/48814 | | 6/1997 |
|---|---|---|---|
| WO | WO 99/04618 | | 7/1998 |
| WO | WO 98/48613 | A1 | 11/1998 |
| WO | WO 00/34491 | | 12/1999 |
| WO | WO 00/58484 | A2 | 10/2000 |
| WO | WO 02/14520 | A2 | 2/2002 |

OTHER PUBLICATIONS

Hansen et al 1999 Trends in Plant Science 4:226-231.*
Potrykus (1990 Biotechnology 8(6): 535-542.*
Cheng et al 1997 Plant Physiology 115:971-980.*
Barro et al 1999 Euphytica 108:161-167.*
Cheng et al, "Genetic transformation of wheat mediated by *Agrobacterium tumefaciens*," Plant Physiology, vol. 115 ( No. 3), p. 971-80, (1997).
McCormac et al., "The use of visual marker genes as cell-specific reporters of *Agrobacterium*-mediated T-DNA delivery wheat (*Triticum aestivum* L.) and barley (*Hordeum vulgare* L.)," Euphytica, vol. 99 ( No. 1), p. 17-25, (1998).

Guo et al, "Factors influencing T-DNA transfer into wheat and barley cells by *Agrobacterium tumefaciens*," Cereal Research Communications, vol. 26 ( No. 1), p. 15-22, (1998).
Trick et al., "Sonication-assisted *Agrobacterium*-mediated transformation," Transgenic Research, vol. 6 ( No. 5), p. 329-36, (1997).
Suzuki et al, "Production of transgenic plants of the Liliiaceous ornamental plant *Agapanthus praecos* ssp. orientalis (Leighton) Leighton via *Agrobacterium*-mediated transformation of embryogenic calli," Plant Science, vol. 161 ( No. 1), p. 89-97, (2001).
Database Biosis, AN: 1998: 375598. Bohoroba et al, "Wheat genetic engineering at CIMMYT," In Vitro Cellular, vol. 34 ( No. 3), p. 55A, (1998).
Database Biosis AN: 1998: 375605. Qingli-Mi et al, "Biolistic and *Agrobacterium*-mediated transformation of wheat and sorghum," In Vitro Cellular, vol. 34 ( No. 3), p. 57A, (1998).
Amrhein et al, "Biochemical basis for glyphosate-tolerance in a bacterium and a plant tissue culture" FEBS Letters, vol. 157(1) p. 191-96, (1983).
Borghouts, C and H.D. Osiewacz, "GRISEA, a copper-modulated transcription factor from *Podospora anserina* involved in senescence and morphogenesis, is an ortholog of MAC1 in *Saccharomyces cerevisiae*," Mol. Gen. Genet., vol. 260 p. 492-502, (1998).
Bregitzer, P et al, "Enhancement of plant regeneration from embryogenic callus of commercial barley cultivars," Plant Cell Reports, vol. 17 p. 941-45, (1998).
Castillo, A.M. et al, "Somatic embryogenesis and plant regeneration from barley cultivars grown in Spain," Plant Cell Reports, vol. 17 p. 902-06, (1998).
Chatfield, J.Mark and Donald J. Armstrong, "Cytokinin oxidase from *Phaseolus vulgaris* callus tissues: Enhanced in vitro activity of the enzyme in the presence of copper-imidazole complexes," Plant Physiol., vol. 84 p. 726-731, (1987).
Dahleen, Lynn S., "Improved plant regeneration from barley callus cultures by increased copper levels," Plant Cell, Tissue and Organ Culture, vol. 43, p. 267-69, (1995).
Ghaemi, Maryann et al, "The effects of silver nitrate, colchicine, cupric sulfate and genotype on the production of embryoids from anthers of tetraploid wheat (*Triticum turgidum*)," Plant Cell, Tissue and Organ Culture, vol. 36 p. 355-59, (1994).
Hare, P.D. and J. Van Staden, "Cytokinin oxidase: biochemical features and physiological significance," Physiologia Plantarium, vol. 91 p. 128-36, (1994).
Harrison, Mark D. et al, "Intracellular copper routing: the role of copper chaperones," TIBS 25 p. 29-32, (2000).
Kim, H.K. et al, "Reduction of genotype limitation in wheat (*Triticum aestivum* L.) transformation," Abstract P-1021, Congress On In Vitro Biology, p. 43-A.
Morard, P. et al, "Kinetics of mineral nutrient uptake by *Saponaria officinalis* L. suspension cell cultures in different media," Plant Cell Reports, vol. 18 p. 260-265, (1998).

(Continued)

Primary Examiner—David T. Fox
Assistant Examiner—Brent T Page
(74) Attorney, Agent, or Firm—Fulbright & Jaworski L.L.P.

(57) ABSTRACT

The present invention relates to an improved transformation and regeneration system for wheat. In particular, the invention relates to enhancements in the glyphosate selection system. The transformation method is efficient and reliable for production of fertile plants with improved agronomic qualities.

7 Claims, 3 Drawing Sheets

OTHER PUBLICATIONS

Morillo, Esmeralda et al, "Adsorption of glyphosate on the clay mineral montmorillonite: effect of Cu(II) in solution and adsorbed on the mineral," Environ. Sci. Technol., vol. 31 p. 3588-92, (1997).

Purnhauser, Laszlo and Gyulai Gabor, "Effect of copper on shoot and root regeneration in wheat, triticale, rape and tobacco tissue cultures," Plant Cell, Tissue and Organ Culture, vol. 35 p. 131-39, (1993).

Purnhauser, Laszlo, "Stimulation of shoot and root regeneration in wheat *Triticum aestivum* callus cultures by copper," Cereal Res. Communications, vol. 19 ( No. 4), p. 419-23, (1991).

Shook, Andy L. and Arron C. Guenzi, "Chapter II: Plant regeneration from wheat (*Triticum aestivum* L. cv Bobwhite) callus culutres improved by increasing copper concentration," Thesis, OK State University, p. 20-31, (1996).

Smart et al, "Selective overproduction of 6-enol-Pyruvylshikimic acid 3-phosphate synthase in a plant cell culture which tolerates high doses of the herbicide glyphosate," J of Biological Chemstry, vol. 260 (30) p. 16338-46, (1985).

Woeste, Keith E. et al, "Factors regulating ethylene biosynthesis in etiolated *Arabidopsis thaliana* seedlings," Physiologia Plantarum, vol. 105 p. 478-84, (1999).

Zhang, S. et al, "Genetic transformation of commercial cultivars of oat (*Avena sativa* L.) and barley (*Hordeum vulgare* L.) using in vitro shoot meristematic cultures derived from germinated seedlings," Plant Cell Reports, vol. 18 p. 959-966, (1999).

Zhou, H. et al, "Glyphosate-tolerant CP4 and GOX genes as a selectable marker in wheat transformation," Plant Cell Reports, vol. 15 p. 159-63, (1995).

Hiei et al., "Efficient transformation of rice (*Oryza sativa* L.) mediated by *Agrobacterium* and sequence analysis of the boundaries of the T-DNA," *The Plant Journal*, 6:271-282, 1994.

Ishida et al., "High efficiency transformation of maize (*Zea mays* L.) mediated by *Agrobacterium tumefaciens,*" *Nature Biotechnology*, 14:745-750, 1996.

Raineri et al., "*Agrobacterium*-mediated transformation of rice (*Oryza sativa* L.)," *Biotechnology*, 8:33-38, 1990.

Tingay et al., "*Agrobacterium tumefaciens*-mediated barley transformation," *The Plant Journal*, 11:1369-1376, 1997.

* cited by examiner

EFFICIENCY *AGROBACTERIUM*-MEDIATED WHEAT TRANSFORMATION METHOD

BACKGROUND OF INVENTION

This application claims priority to U.S. provisional application 60/314,087, filed Aug. 22, 2001, herein incorporated by reference in its entirety.

The present invention relates to the field of plant biotechnology. More specifically, it concerns methods and conditions for improved *Agrobacterium*-mediated transformation of regenerable wheat cells or tissues.

During the past decade, it has become possible to transfer genes from a wide range of organisms to crop plants by recombinant DNA technology. This advance has provided enormous opportunities to improve plant resistance to pests, disease and herbicides, and to modify biosynthetic processes to change the quality of plant products (Knutson et al., 1992; Piorer et al., 1992; Vasil et al., 1992). The lack of efficient *Agrobacterium*-mediated transformation methods suitable for high capacity production of economically important plants has limited this potential opportunity.

Initially, monocot species were transformed via microprojectile bombardment methods. Microprojectile bombardment has several disadvantages including fragmenting of the inserted DNA, insertion of multiple copies, and reduced efficiency. More recently, monocot species have been successfully transformed via *Agrobacterium*-mediated transformation. Thus, *Agrobacterium*-mediated transformation provides a viable alternative to microprojectile bombardment methods.

Notwithstanding the availability of *Agrobacterium*-mediated transformation methods in the art, there still remains a need for improved methods that permit transformation on production level scale and efficiencies. The present invention provides such an improvement of an *Agrobacterium*-mediated transformation method. The method is more efficient in delivering target DNA to the plant and more efficient in selecting transformed plants as evidenced by higher transformation efficiencies. Moreover, the present method provides a reduction in labor and cost advantage as compared to conventional methods.

SUMMARY OF INVENTION

The present invention relates to improved methods of *Agrobacterium*-mediated transformation for monocots, particularly wheat.

In one aspect of this invention, the invention relates to a method for transforming monocotyledonous plants using an *Agrobacterium*-mediated process comprising the steps of preculturing at least one immature embryo from a monocotyledonous plant in a first medium containing increased MS salts and increased picloram; contacting the precultured embryo with *Agrobacterium* capable of transferring at least one gene construct to the embryo; co-cultivating the embryo with *Agrobacterium*; culturing the embryo in a second medium containing a selective agent to select for embryos expressing the gene construct; and regenerating plants expressing the gene construct. This invention also relates to cells transformed by and plants regenerated by this method.

In another aspect of this invention, the invention relates to a method for transforming monocotyledonous plants using an *Agrobacterium*-mediated process comprising the steps of preculturing at least one immature embryo from a monocotyledonous plant in a medium containing a concentration of glyphosate insufficient to kill cells; contacting the precultured embryo with *Agrobacterium* capable of transferring at least one gene construct to the embryo in which at least one gene is a gene that confers resistance to a glyphosate-containing herbicide; co-cultivating the embryo with *Agrobacterium*; culturing the embryo in a first medium containing a concentration of glyphosate that is not sufficient to kill cells; culturing the embryo in a second medium containing a selective amount of glyphosate to select for embryos expressing the gene construct; and regenerating plants expressing the gene construct. The invention also relates to plants regenerated by this method and to cells transformed by this method.

In yet another aspect of this invention, a method is disclosed for transforming monocotyledonous plants using an *Agrobacterium*-mediated process comprising the steps of preculturing at least one immature embryo from a monocotyledonous plant; contacting the precultured embryo with *Agrobacterium* capable of transferring at least one gene construct to the embryo in which at least one gene is a gene that confers resistance to a glyphosate-containing herbicide; co-cultivating the embryo with *Agrobacterium*; culturing the embryo in a medium containing aromatic amino acids and a selective amount of glyphosate to select for embryos expressing the gene construct; and regenerating plants expressing the gene construct. Plants regenerated by this method and cells transformed by this method are also envisioned within this invention.

In yet another aspect of this invention, a method is disclosed for transforming monocotyledonous plants using an *Agrobacterium*-mediated process comprising the steps of preculturing at least one immature embryo from a monocotyledonous plant; contacting the precultured embryo with *Agrobacterium* capable of transferring at least one gene construct to the embryo; co-cultivating the embryo with *Agrobacterium*; culturing the embryo in a first medium containing a selective agent to select for embryos expressing the gene construct; and regenerating plants expressing the gene construct in a second medium containing an effective amount of copper. This invention also relates to plants regenerated by this method and to cells transformed by this method.

In a preferred aspect of this invention, the invention relates to a method for transforming monocotyledonous plants using an *Agrobacterium*-mediated process comprising the steps of preculturing at least one immature embryo from a monocotyledonous plant in a first medium containing increased MS salts, increased picloram, and a concentration of glyphosate insufficient to kill cells; contacting the precultured embryo with *Agrobacterium* capable of transferring at least one gene construct to the embryo including a gene that confers glyphosate resistance; co-cultivating the embryo with *Agrobacterium*; culturing the embryo in a second medium containing a concentration of glyphosate insufficient to kill cells; culturing the embryo in a third medium containing aromatic amino acids and a selective amount of glyphosate to select for embryos expressing the gene construct; and regenerating plants expressing the gene construct in a fourth medium containing an effective amount of copper. This invention also relates to plants regenerated by this method and to cells transformed by this method.

DETAILED DESCRIPTION

Figure 1:
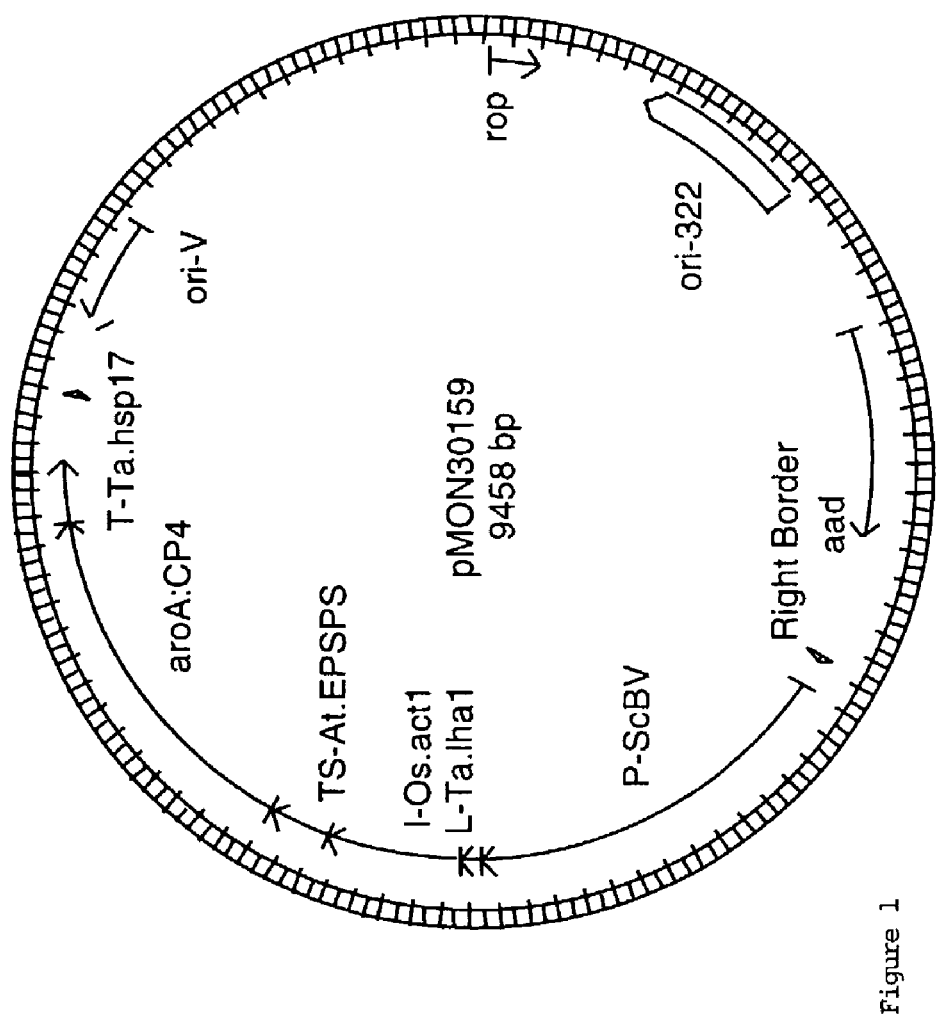
FIG. 1 is a plasmid map of pMON30159.
Figure 2:
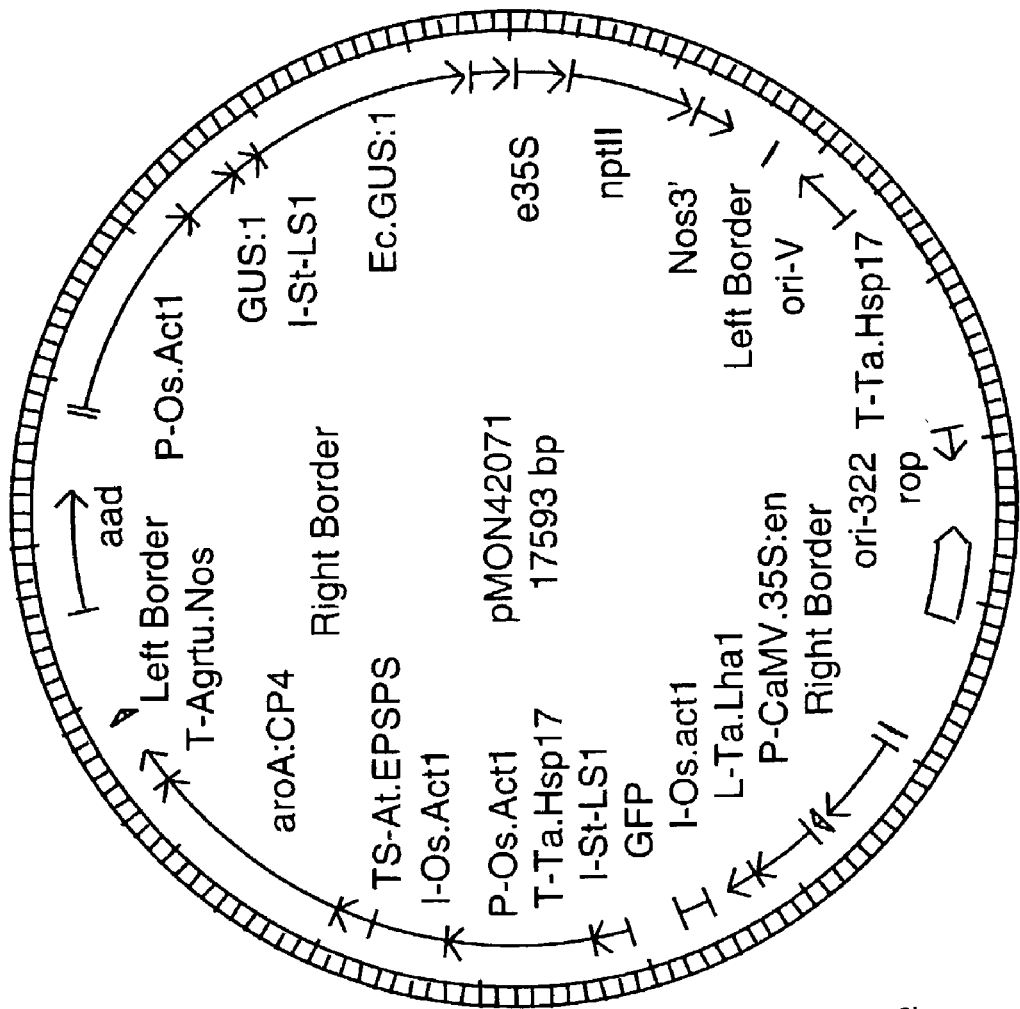
FIG. 2 is a plasmid map of pMON42071.
Figure 3:
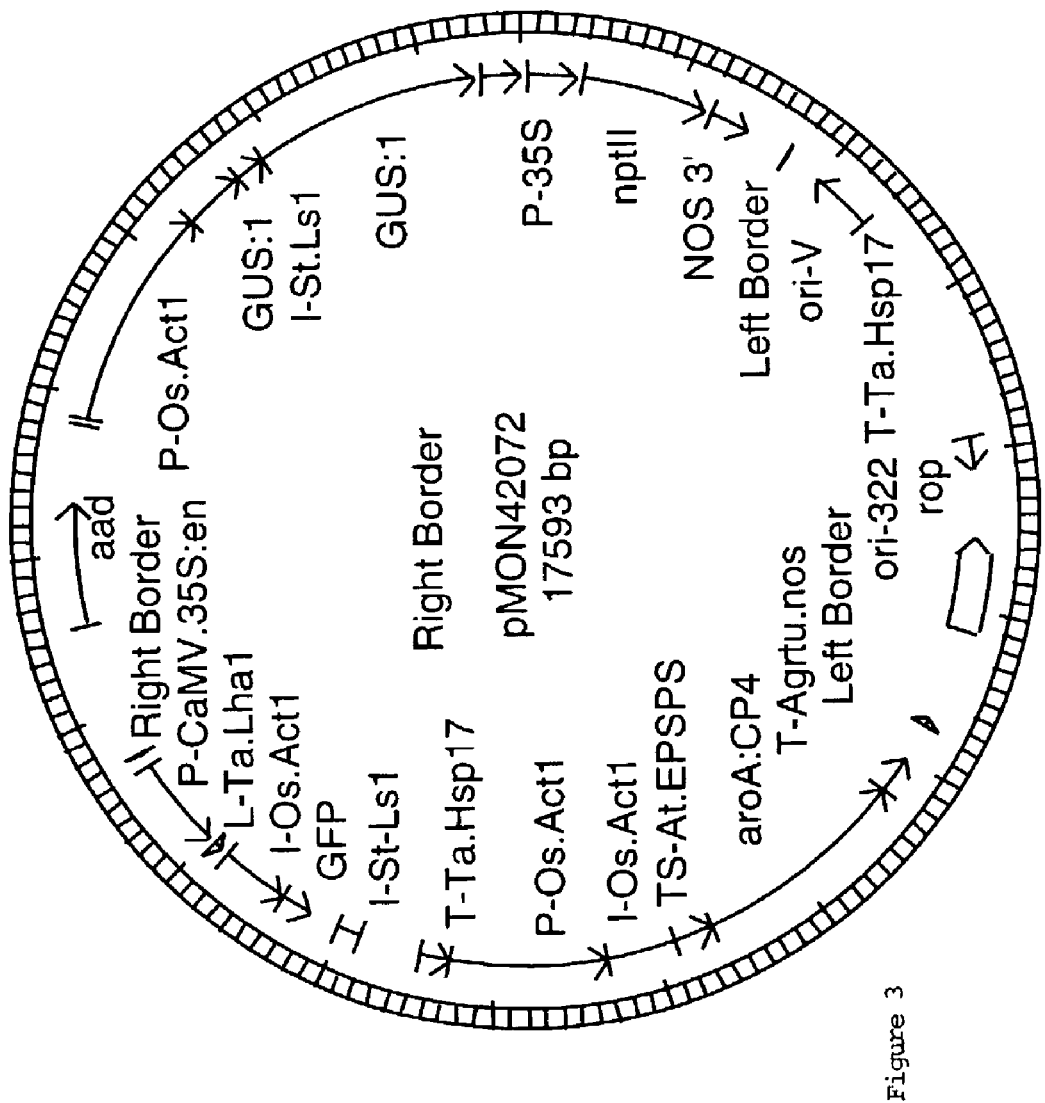
FIG. 3 is a plasmid map of pMON42072.

The present invention provides a fertile transgenic plant and a method for transformation of plant cells or tissues and regeneration of the transformed cells or tissues into a differentiated transformed plant. In other aspects, the invention relates to the production of stable transformed and fertile plants, gametes, and offspring from these plants. The present invention applies to monocots, such as corn, rice, barley, and wheat. To initiate a transformation process in accordance with the present invention, it is first necessary to select genetic components, gene constructs, or genes to be inserted into the plant cells or tissues. Gene constructs may include any nucleic acid that is introduced into a plant cell or tissue using the method according to the invention. Gene constructs may include non-plant DNA, plant DNA, or synthetic DNA.

In an embodiment, genetic components are incorporated into a DNA composition or gene construct such as a recombinant, double-stranded plasmid or vector molecule comprising at least one or more of the following types of genetic components: (a) a promoter that functions in plant cells to cause the production of an RNA sequence, (b) a structural DNA, sequence that causes the production of an RNA sequence that encodes a product of agronomic utility, (c) a 3" non-translated DNA sequence that functions in plant cells to cause the addition of polyadenylated nucleotides to the 3" end of the RNA sequence. The vector may contain a number of genetic components or gene constructs to facilitate transformation of the plant cell or tissue and regulate expression of the desired gene(s).

In one embodiment, the gene constructs are oriented so as to express a mRNA, which in one embodiment can be translated into a protein. The expression of a plant structural coding sequence (a gene, cDNA, synthetic DNA, or other DNA) that exists in double-stranded form involves transcription of messenger RNA (mRNA) from one strand of the DNA by RNA polymerase enzyme and subsequent processing of the mRNA primary transcript inside the nucleus. This processing involves a 3" non-translated region that adds polyadenylated nucleotides to the 3" ends of the mRNA.

Means for preparing plasmids or vectors containing the desired gene constructs are well known in the art. Vectors used to transform plants and methods of making those vectors are described in U.S. Pat. Nos. 4,971,908, 4,940,835, 4,769,061 and 4,757,011, the entirety of which are incorporated herein by reference. Vectors typically consist of a number of genetic components, including but not limited to regulatory elements such as promoters, leaders, introns, and terminator sequences. Regulatory elements are also referred to as cis- or trans-regulatory elements, depending on the proximity of the element to the sequences or gene(s) they control.

Transcription of DNA into mRNA is regulated by a region of DNA usually referred to as the "promoter." The promoter region contains a sequence of bases that signals RNA polymerase to associate with the DNA and to initiate the transcription into mRNA using one of the DNA strands as a template to make a corresponding complementary strand of RNA.

A number of promoters that are active in plant cells have been described in the literature. Such promoters would include, but are not limited to, the nopaline synthase (NOS) and octopine synthase (OCS) promoters, which are carried on tumor-inducing plasmids of *Agrobacterium tumefaciens;* the caulimovirus promoters such as the cauliflower mosaic virus (CaMV) 19S and 35S promoters and the figwort mosaic virus (FMV) 35S promoter; the enhanced CaMV35S promoter (e35S); and the light-inducible promoter from the small subunit of ribulose bisphosphate carboxylase (ss-RUBISCO, a very abundant plant polypeptide). All of these promoters have been used to create various types of DNA constructs that have been expressed in plants. See, for example, PCT publication WO 84/02913.

Promoter hybrids can also be constructed to enhance transcriptional activity (U.S. Pat. No. 5,106,739) or to combine desired transcriptional activity, inducibility, and tissue or developmental specificity. Promoters that function in plants are promoters that are inducible, viral, synthetic, constitutive as described (Poszkowski et al., 1989; Odell et al., 1985), and temporally regulated, spatially regulated, and spatio-temporally regulated (Chau et al., 1989). Other promoters that are tissue-enhanced, tissue-specific, or developmentally regulated are also known in the art and envisioned to have utility in the practice of this invention. Promoters may be obtained from a variety of sources such as plants and plant DNA viruses and include, but are not limited to, the CaMV35S and FMV35S promoters and promoters isolated from plant genes such as ssRUBISCO genes. As described below, it is preferred that the particular promoter selected should be capable of causing sufficient expression to result in the production of an effective amount of the gene product of interest.

The promoters used in the DNA constructs (i.e., chimeric/recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression. Examples of such enhancer sequences have been reported by Kay et al. (1987).

The mRNA produced by a DNA construct of the present invention may also contain a 5' non-translated leader sequence. This sequence can be derived from the promoter selected to express the gene and can be specifically modified so as to increase translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA. The present invention is not limited to constructs wherein the non-translated region is derived from the 5' non-translated sequence that accompanies the promoter sequence. Rather, the non-translated leader sequence can be derived from unrelated promoters or genes (see, for example U.S. Pat. No. 5,362,865). Other genetic components that serve to enhance expression or affect transcription or translation of a gene are also envisioned as gene constructs. The 3' non-translated region of the chimeric constructs should contain a transcriptional terminator, or an element having equivalent function, and a polyadenylation signal, which functions in plants to cause the addition of polyadenylated nucleotides to the 3' end of the RNA. Examples of suitable 3' regions are (1) the 3' transcribed, non-translated regions containing the polyadenylation signal of *Agrobacterium* tumor-inducing (Ti) plasmid genes, such as the nopaline synthase (NOS) gene, and (2) plant genes such as the soybean storage protein genes and the small subunit of the ribulose-1,5-bisphosphate carboxylase (ssRUBISCO) gene. An example of a preferred 3' region is that from the ssRUBISCO E9 gene from pea (European Patent Application 385,962, herein incorporated by reference in its entirety).

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

In one embodiment of the present invention, the vector contains a selectable, screenable, or scoreable marker gene. These genetic components are also referred to herein as functional genetic components, as they produce a product that serves a function in the identification of a transformed plant, or a product of desired utility. The DNA that serves as a selection device functions in a regenerable plant tissue to produce a compound that would confer upon the plant tissue resistance to an otherwise toxic compound. Genes of interest for use as a selectable, screenable, or scorable marker would include, but are not limited to, β-glucuronidase (GUS), green fluorescent protein (GFP), luciferase (LUX), antibiotic or herbicide tolerance genes. Examples of antibiotic resistance genes include the genes for resistance to penicillins; kanamycin (and neomycin, G418, bleomycin); methotrexate (and trimethoprim); chloramphenicol; and tetracycline.

A number of selectable marker genes are known in the art. Particularly useful selectable marker genes for use in the present invention are genes that confer resistance to glyphosate (Della-Cioppa et al., 1987).

The present invention can be used with any suitable plant transformation plasmid or vector containing a selectable marker and associated regulatory elements as described, along with one or more nucleic acids expressed in a manner sufficient to confer a particular desirable trait. Examples of suitable structural genes of interest envisioned by the present invention would include, but are not limited to, genes for insect or pest tolerance, herbicide tolerance, genes for quality improvements such as yield, nutritional enhancements, environmental or stress tolerances, or any desirable changes in plant physiology, growth, development, morphology, or plant product(s).

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see, for example, Gibson and Shillitoe, 1997). Thus, any gene that produces a protein or mRNA that expresses a phenotype or morphology change of interest is useful for the practice of the present invention.

Exemplary nucleic acids that may be introduced by the methods encompassed by the present invention include, for example, DNA sequences or genes from another species, or even genes or sequences that originate with or are present in the same species but are incorporated into recipient cells by genetic engineering methods rather than classical reproduction or breeding techniques. However, the term exogenous is also intended to refer to genes that are not normally present in the cell being transformed or to genes that are not present in the form, structure, etc., as found in the transforming DNA segment or to genes that are normally present but a different expression is desirable. Thus, the term "exogenous" gene or DNA is intended to refer to any gene or DNA segment that is introduced into a recipient cell, regardless of whether a similar gene may already be present in such a cell.

The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

In light of this disclosure, numerous other possible regulatory elements and other sequences of interest will be apparent to those of skill in the art. Therefore, the foregoing discussion is intended to be exemplary rather than exhaustive.

After the construction of the plant transformation vector or construct, said nucleic acid molecule, prepared as a DNA composition in vitro, can be introduced into a suitable host such as *E. coli* and mated into another suitable host such as *Agrobacterium*, or directly transformed into competent Agrobacteria. These techniques are well-known to those of skill in the art and have been described for a number of plant systems including soybean, cotton, and wheat (see, for example, U.S. Pat. Nos. 5,569,834 and 5,159,135 and WO 97/48814 herein incorporated by reference in their entirety). The present invention encompasses the use of bacterial strains to introduce one or more genetic components into plants. Those of skill in the art would recognize the utility of *Agrobacterium*-mediated transformation methods. Preferred strains could include, but are not limited to, *Agrobacterium tumefaciens* strain C58, a nopaline strain that is used to mediate the transfer of DNA into a plant cell; octopine strains, such as LBA4404; or agropine strains, e.g., EHA101, EHA105, or EHA109. The use of these strains for plant transformation has been reported, and the methods are familiar to those of skill in the art.

The present invention can be used with immature embryos isolated from wheat spikelets. The isolation of wheat immature embryos is described by Weeks et al. (1993) and Vasil et al. (1993) and in WO 97/48814. An embodiment of the present invention is to use precultured cells or tissues as the starting material. Precultured, as used herein, means culturing the cells or tissues in an appropriate medium to support plant tissue growth prior to inoculation with *Agrobacterium*. The preculture of the regenerable cells or tissue prior to *Agrobacterium* inoculation can occur for an extended period of time, for example seven days or more. The preculture period could also be for six days or less. Also, the preculture period could be a shorter period of time such as about one hour to four days. Examples of suitable media for preculture would include, but are not limited to, MS-based media (Murashige and Skoog, 1962) or N6-based media (Chu et al., 1978) supplemented with additional nutrients and/or plant growth regulators including, but not limited to, picloram and 2,4-D (see Table 2). The preculture media also could be CM4C (which contains the standard amount of MS salts) (Table 2), and, for example, could be CM4C with an increased amount of MS salts and an increased amount of picloram, and also could be M7 (CM4C with double the amount of MS salts and 4 mg/L picloram). The amount of MS salts can be increased from about 1.5- to 3-fold, or for example 2-fold. The amount of picloram can be increased to from about 3 mg/L to 5 mg/L, or for example to about 4 mg/L.

Those of skill in the art are familiar with the variety of tissue culture media that, when supplemented appropriately, support plant tissue growth and development. These tissue culture media can either be purchased as a commercial preparation or custom prepared and modified by those of skill in the art. Examples of such media would include, but are not limited to, Gamborg's media (Gamborg et al., 1968), McCown's Woody plant media (McCown and Lloyd, 1981), Nitsch and Nitsch media (Nitsch and Nitsch, 1969), and Schenk and Hildebrandt media (Schenk and Hildebrandt, 1972) supplemented accordingly. Those of skill in the art are aware that media and media supplements such as nutrients and growth regulators for use in transformation and regeneration are usually optimized for the particular target crop or variety of interest. Many aspects of the current invention can be combined with a variety of media to achieve similar effects, and such combinations are considered part of the current invention.

Also in the preculture media, in a further embodiment of the invention, a level of glyphosate that is insufficient to kill plant cells is included in the preculture media, for example from about 0.001 to 0.2 mM, or from about 0.005 to 0.05 mM, or about 0.02 mM. One of skill in the art realizes that the amount of time in precultured can influence the concentration of glyphosate that is useful. The higher concentrations are more appropriate for shorter periods of time, whereas the lower concentrations are more useful for longer periods of time. The precultured step is generally performed at about 20° C. to about 28° C.; however, in some varieties it has been found useful to preculture at about 32° C.

Once the regenerable plant tissue is isolated, the next step of the method is introducing the genetic components into the plant tissue. This process is also referred to herein as "transformation." The plant cells are transformed and each independently transformed plant cell is selected. The independent transformants are referred to as plant cell lines.

The *Agrobacterium* strain harboring the plasmid or vector of interest is cultured on an appropriate culture medium, such as Luria Burtani (LB) supplemented with selective antibiotics for the strain and vector. Those of skill in the art are familiar with procedures for growth and suitable culture conditions for *Agrobacterium* as well as subsequent inoculation procedures. The density of the *Agrobacterium* culture used for inoculation and the ratio of *Agrobacterium* cells to explant can vary from one system to the next, and therefore optimization of these parameters for any transformation method is expected. Typically, an *Agrobacterium* culture is inoculated from a streaked plate or glycerol stock and is grown overnight and the bacterial cells are washed and resuspended in a culture medium suitable for inoculation of the explant. Suitable inoculation media for the present invention include, but are not limited to, 1/10 MS salts in CM4C media (Table 2) or a modified CM4C culture medium with a reduced salt concentration.

In some cases, a surfactant including, but not limited to, Silwet L77 (Wites, Hudson, Ohio) or pluronic F68 (Sigma, St. Louis, Mo.) may also be added to the inoculation medium at a low concentration. Any surfactant compatible with the method of the instant invention may be used. The surfactant is used at concentrations of about 0.001% (v/v) to about 0.1% (v/v) in solution. It may also be used at concentrations of about 0.005% (v/v) to about 0.08% (v/v) in solution, or it may be used at a concentration of about 0.01% (v/v) in solution.

The explants are incubated with the washed and resuspended *Agrobacterium* cell suspension. The inoculation is generally performed at a temperature of about 20° C.–28° C. or about 23° C.–28° C. or from about 24° C. to about 26° C. or at 25° C. from about 1 minute to about 3 hours.

The inoculated explant may be treated such that the weight of the explant is reduced during the co-culture period. One method of decreasing the weight of the *Agrobacterium*-inoculated explant may be to limit the moisture supply to said explant during co-culture as described by Cheng and Fry in WO 2000/034491, herein incorporated in its entirety by reference. Co-culture, as used herein, means the time from when the explant is inoculated with the *Agrobacterium* culture up to the transfer to delay media or selection media (if there is no delay media). The *Agrobacterium*-inoculated explant is placed in a tissue culture vessel such as a petri plate that does not contain media containing a gelling agent. In one embodiment, the explant is placed on a suitable blotting material, including, but not limited to, filter paper that is placed in the petri plate.

After the co-culture period, the *Agrobacterium*-inoculated explants are cultured on an appropriate delay medium containing an agent to inhibit *Agrobacterium* growth. The *Agrobacterium*-inoculated explants are cultured on such a media generally from one to fourteen days or from two to seven days. Those of skill in the art are aware of the appropriate media components to inhibit *Agrobacterium* growth. Such media components would include, but are not limited to, antibiotics such as carbenicillin or cefotaxime. The media at this stage also could contain a level of glyphosate insufficient to kill plant cells, for example from about 0.001 to 0.1 mM or from about 0.005 to 0.05 mM or about 0.02 mM. In another embodiment, after incubation on media containing the antibiotics to inhibit *Agrobacterium* growth with a level of selective agent insufficient to kill plant cells, the explants are cultured on selective growth media including, but not limited to, a callus—inducing media containing the selective agent glyphosate. At the selection stage, the selection agent can be present in a selective amount sufficient to provide an advantage for cells that have been transformed with the gene that confers resistance and that then express that gene.

Glyphosate is a broad spectrum herbicide that is extremely effective in disruption of biosynthesis of aromatic amino acids: the main source of vitamins, auxins, lignins, anthocyanins, etc., that are vitally important for life and growth of plants. Addition of 60 μM (10 mg/L) of a mixture of three aromatic amino acids (AAA): tyrosine (tyr), phenylalanine (phe), and tryptophan (trp) on *Aerobacter aerogenes* (*Klebsiella pneumoniae*) (Amrhein et al., 1983) and of 500 μM of the mixture on the suspension cultured cells of *Corydalis sempervirens* Pers. (Smart et al., 1985) completely prevented inhibitory effect of glyphosate on the cultures. The previous protocol (as discussed in Example 15) included the addition of phe, tyr, and trp each at concentration of 0.1 μM (that is 600–5000 times less in comparison to above mentioned references) at "2nd regeneration stage" (MMS0C media), which is characterized by the appearance of small green shoots on embryogenic calluses.

After the selection stage, plant material goes through a 1st regeneration stage followed by a $2^{nd}$ regeneration stage to produce plants. In an embodiment of the invention, AAA can be added to the culture media at "selection stage" (CM4C), "1 st regeneration stage" (MMS0.2C), and "2nd regeneration stage" (MMS0C) of the protocol. The presence of very low concentrations (0.1 μM) of tyr, phe, and trp during formation of embryogenic cell clusters and somatic embryos could give a selective advantage to transformed cells resistant to glyphosate. Those cells are likely to be highly meristematic and regenerable, being the primary target for glyphosate action, as it is known that glyphosate tends to accumulate in meristematic cells and tissues (Franz et al., 1997). On the other hand, this very low 0.1 μM concentration of AAA still should not be strong enough to reverse the inhibitory effect of glyphosate in non-transformed cells.

Therefore, the mixture of the three aromatic amino acids in the media could be from about 0.001 μM to 100 μM or from about 0.01 μM to 10 μM or about 0.1 μM.

The cultures can be subsequently transferred to a regeneration media suitable for the production of transformed plantlets. Regeneration is typically done in two different media. The first media also contains the aromatic amino acids. The second media can contain the aromatic amino acids as described above and also copper, for example from about 0.5 µM to 3 mM or from about 1 µM to 100 µM or from about 2 to 20 µM. Copper improves wheat regeneration in general not just as part of glyphosate selection. Copper can be in the media as copper sulfate, copper chloride, copper nitrate or copper acetate, but other copper salts should work as well. Zinc sulfate, nickel sulfate, cobalt chloride, iron sulfate or sulfite, chelated iron (Fe-EDDHA), manganese sulfate, magnesium chloride or similar salts would also be expected to have a similar effect.

Copper (Cu) is a transition metal ion that could be involved in photosynthesis, ATP-, lignin-, and ethylene-biosynthesis (Woeste et al., 1999). By studying mineral nutrient uptake in soapwort suspension cells, it was found that copper had been depleted from the MS based culture media by day 8 (Morard et al., 1998), suggesting that more attention should be given to constant copper supply in tissue culture media. Copper has a potential to bind glyphosate (Morillo et al., 1997) and probably agar as well in tissue culture media in a pH-dependent manner. Thus higher concentrations of both copper and glyphosate might be effective for improved selection of transgenic plants in the presence of glyphosate.

The positive effect of copper on wheat regeneration was demonstrated first in 1991 (Purnhauser, 1991). Later on the stimulatory effect of copper on plant regeneration from callus cultures of several barley and wheat species was shown (Purnhauser & Gyulai, 1993; Ghaemi et al., 1994; Dahleen, 1995; Shook and Guenzi, 1996; Bregitzer et al., 1998; Castillo et al., 1998). It has been reported (Kim et al, 1999; WO 98/48613) that Cu in addition to other factors improved regeneration and transformation efficiency of recalcitrant spring wheat genotypes. These groups all used copper early in the regeneration process, whereas the present invention shows a greater effect later in the regeneration process. The present invention can have copper in the second regeneration medium, for example from about 0.5 µM to 3 mM or from about 1 µM to 100 µM or from about 2 to 20 µM. Effects of copper are independent of transformation or selection methods. Thus addition of copper in regeneration should be beneficial in any selection system or in any transformation system, such as, but not limited to, microparticle bombardment.

Preculture, co-culture, delay and selection can be performed at a temperature of about 20° C.–28° C. or about 23° C.–28° C. or from about 24° C. to about 26° C. or at 25° C. Selection is done for about 3 to 15 days or from 7 to 12 days or for 10 days.

Those of skill in the art are aware of the numerous types of media and transfer requirements that can be implemented and optimized for each plant system for plant transformation and regeneration. Consequently, such media and culture conditions disclosed in the present invention can be modified or substituted with nutritionally equivalent components, or similar processes for selection and regeneration, and still fall within the scope of the present invention.

The transformants produced are subsequently analyzed to determine the presence or absence of a particular nucleic acid of interest contained on the transformation vector. Molecular analyses can include, but are not limited to, Southern blots (Southern, 1975) or PCR (polymerase chain reaction) analyses. These and other well known methods can be performed to confirm the stability of the transformed plants produced by the methods disclosed. These methods are well known to those of skill in the art and have been reported (see, for example, Sambrook et al., (1989).

Those of skill in the art will appreciate the many advantages of the methods and compositions provided by the present invention. The following examples are included to demonstrate the preferred embodiments of the invention. It should be appreciated by those of skill in the art that the techniques disclosed in the examples represent techniques discovered by the inventors to function well in the practice of the invention and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Plasmid Vector Construction

Plasmid vectors were constructed using standard molecular biological techniques known to one of ordinary skill in the art. A number of *Agrobacterium*-mediated plant transformation vectors have been described (Klee and Rogers, 1989). Briefly, the plant transformation vectors described herein comprise one or more nucleic acid sequences including but not limited to one or more T-DNA border sequences to promote the transfer of nucleic acid molecules into the plant genome, replication elements, a selectable marker gene for glyphosate and one or more gene(s) of interest. The basic features of the vectors used in the Examples are summarized in Table 1 and are listed as follows: promoter/coding sequence/3"-untranslated region.

The abbreviations in the table are described as follows: The CaMV.35S:en (e35S) promoter is a modification of the 35S promoter derived from the 35S RNA of cauliflower mosaic virus (CaMV) which contains a duplication of the −90 to −300 region; The Os.Act1 promoter is from the rice actin 1 gene, including the promoter, the 5" UTR, and the first intron. The SCBV promoter is from sugarcane badnavirus and also includes the first rice actin intron (I-Os.act1). The L-Ta.Lha1 is the leader sequence from the wheat CAB gene. The GUS gene is the β-glucuronidase coding sequence from *E. coli;* The nptII gene codes for neomycin phosphotransferase; The CP4 gene codes for glyphosate resistance; the T.Agrtu.nos (nos3' region contains downstream untranslated sequence and the poly A signal for the NOS gene of *Agrobacterium tumefaciens* pTiT37; and the T-Ta.Hsp17 is the 3" region of the wheat heat shock protein 17. All elements are named using current conventions in the art as found at genome-www.stanford.edu/mendel.

[t2]

TABLE 1

Plasmid Vectors

| Plasmid | Genetic Elements |
| --- | --- |
| pMON30159 | P-SCBV-aroA. CP4-T-Ta.Hsp17 |
| pMON42071 | P-CaMV 35S:en-nptII-T-Agrtu nos/pCaMV 35S en-I-Os Act1-GFP-T-Ta.Hsp17/P-Os Act1-CP4-T-Agrtu nos/P-Os Act1-GUS-T-Ta.Hsp17 |
| pMON42072 | P-Os Act1-GUS-T-Ta Hsp17/P-CaMV 35S.en-nptII-T-Agrtu nos/P-Os Act1-CP4-T-Agrtu nos/P-CaMV 35S en-I-Os.Act1-GEP-T-Ta Hsp17 |

Example 2

Transformation Using Precultured Immature Embryos (PCIEs) of Wheat Explant Preparation Immature embryos of wheat (*Triticum aestivum* L) cv Bobwhite were isolated from the immature caryopsis (wheat spikelets) 12–15 days after pollination, and cultured on CM4C (Table 2) for 1–8 days, most typically for 4–6. The embryos without embryogenic callus were selected for *Agrobacterium* inoculation.

TABLE 2

Supplemental Components in Basal Media[1]

| Components | CM4 | CM4C | MMS0 2C | MMS0C |
|---|---|---|---|---|
| 2,4-D(mg/L) | 0.5 | 0.5 | 0.2 | — |
| Picloram (mg/L)[2] | | 2.4 | 2.4 | |
| Maltose (g/L) | 40.0 | 40.0 | 40.0 | 40.0 |
| Glutamine (g/L) | | 0.5 | 0.5 | |
| Magnesium Chloride (g/L) | | 0.75 | 0.75 | |
| Casein Hydrolysate (g/L) | | | 0.1 | 0.1 |
| MES (g/L) | | 1.95 | 1.95 | 1.95 |
| Ascorbic Acid (mg/L)[2] | | 100.0 | 100.0 | 100.0 |
| Gelling Agent (g/L)[3] | 2(P) | 2(P) | 2(G) | 2(G) |

[1]All media contain basal salts (MS basal salts) and vitamins (MS vitamins) from Murashige and Skoog (1962) The pH in each medium was adjusted to 5.8.
[2]Filter-sterilized and added to the medium after autoclaving.
[3]PHYTAGEL (P) (PHYTAGEL is a regsitered trademark of Sigma Chemical Co., St Louis, MO) or GELRITE (G) (GELRITE is available from Schweizerhall, Inc, South Plainfield NJ) (GELRITE is a registered trademark of Monsanto Company, St. Louis, MO)

Example 3

Use of M7 Medium for Preculture

M7 medium was based on the regular preculture medium CM4C, but the amount of MS salts was doubled from the standard concentration and the picloram concentration was increased from 2.4 mg/L to 4 mg/L. The results from the experiments of both selection on glyphosate and selection with nptII(see Example 13) showed that better embryogenic callus was produced and the efficiency was increased when immature embryos were precultured on M7 medium (Tables 3a and 3b).

TABLE 3a

Improvement of transformation efficiency of using M7 medium with glyphosate selection

| Exp. | Treatments | Embryo # | Events | Efficiency % |
|---|---|---|---|---|
| 1 | Control | 250 | 8 | 3.2 |
| 1 | M7 | 250 | 21 | 8.4 |
| 2 | Control | 250 | 19 | 7.6 |
| 2 | M7 | 250 | 20 | 8.0 |
| 3 | Control | 200 | 9 | 4.5 |
| 3 | M7 | 300 | 25 | 8.33 |
| 4 | Control | 270 | 13 | 4.8 |
| 4 | M7 | 245 | 10 | 4.08 |
| 5 | Control | 240 | 3 | 1.25 |
| 5 | M7 | 360 | 18 | 5 |
| 6 | Control | 300 | 5 | 1.67 |
| 6 | M7 | 300 | 6 | 2.00 |
| 7 | Control | 82 | 1 | 1.22 |
| 7 | M7 | 187 | 7 | 3.74 |
| 8 | Control | 70 | 0 | 0 |
| 8 | M7 | 75 | 4 | 5.3 |
| 9 | Control | 150 | 8 | 5.3 |
| 9 | M7 | 150 | 8 | 5.3 |
| 10 | Control | 260 | 1 | 0.3 |
| 10 | M7 | 180 | 13 | 7.2 |
| 11 | Control | 300 | 12 | 4 |
| 11 | M7 | 300 | 19 | 6.3 |
| Total | Control | 2372 | 79 | 3.3 |
| | M7 | 2597 | 151 | 5.8 |

TABLE 3b

Improvement of transformation efficiency of using M7 medium with kanamycin selection

| Exp. | Treatments | Embryo # | Events | TE % |
|---|---|---|---|---|
| 1 | Control | 266 | 5 | 1.88 |
| 1 | M7 | 136 | 11 | 8.09 |
| 2 | Control | 175 | 5 | 2.86 |
| 2 | M7 | 116 | 8 | 6.9 |
| 3 | Control | 379 | 8 | 2.11 |
| 3 | M7 | 155 | 6 | 3.87 |
| 4 | Control | 329 | 30 | 9.12 |
| 4 | M7 | 125 | 22 | 17.6 |
| 5 | Control | 106 | 2 | 1.89 |
| 5 | M7 | 92 | 7 | 7.61 |
| 6 | Control | 210 | 13 | 6.19 |
| 6 | M7 | 210 | 18 | 8.57 |
| 7 | Control | 211 | 3 | 1.42 |
| 7 | M7 | 219 | 7 | 3.2 |
| 8 | Control | 205 | 7 | 3.41 |
| 8 | M7 | 202 | 29 | 14.36 |
| 9 | Control | 223 | 12 | 5.38 |
| 9 | M7 | 289 | 16 | 5.54 |
| Total | Control | 2104 | 85 | 4.03 |
| | M7 | 1544 | 124 | 8.3 |

Example 4

Addition of Glyphosate in the Preculture Medium and Delay Culture Medium

It was found to be beneficial to add low levels of glyphosate that are not sufficient to kill cells to the preculture and delay culture media. In these experiments, when glyphosate at 0.02 mM was added into the preculture and delay culture media, the transformation efficiency was significantly improved (Table 4).

TABLE 4

Effects of addition of 0.02 mM glyphosate in preculture and delay culture media

| Exp. | Treatments | Embryo # | Events | TE % |
|---|---|---|---|---|
| 1 | CM4C | 195 | 6 | 3.0 |
| 1 | CM4C + 0.02 mM gly | 205 | 17 | 8.3 |
| 2 | CM4C | 235 | 7 | 3.0 |
| 2 | CM4C + 0.02 mM gly | 245 | 11 | 2.4 |
| 3 | CM4C | 298 | 8 | 2.7 |
| 3 | CM4C + 0.02 mM gly | 297 | 11 | 3.7 |
| 4 | CM4C | 240 | 5 | 2.1 |
| 4 | CM4C + 0.02 mM gly | 240 | 9 | 3.8 |
| Total | CM4C | 968 | 26 | 2.8 |
| | CM4C + 0.02 mM gly | 981 | 48 | 4.9 |

Example 5

*Agrobacterium* Culture and Inoculation

This example describes an improvement in the preparation of the *Agrobacterium* prior to its use in transformation. A disarmed *Agrobacterium* strain C58 (ABI) harboring a binary vector was used for all the experiments. For the control experiments, cultures of *Agrobacterium* were initiated from glycerol stocks or from a freshly streaked plate and grown overnight at 26° C.–28° C. with shaking (approximately 150 rpm) to mid-log phase (about $OD_{660}$=1–1.5) in liquid LB medium, pH 7.0 (Miller, 1972) containing 50 mg/L kanamycin, 50 mg/L streptomycin and spectinomycin, and 25 mg/L chloramphenicol with 200 µM acetosyringone (AS). The *Agrobacterium* cells were resuspended in the inoculation medium and the density was adjusted to an $OD_{660}$ of 1. The immature embryos cultured in CM4C medium were transferred into sterile petri plates (16×20 mm) or wells of a 6-well cell culture plate (Costar Corporation, Cambridge, Mass.) containing 10 mL of inoculation medium per petri plate or 5 mL per cell culture cluster plate. An equal amount of the *Agrobacterium* cell suspension was added such that the final concentration of *Agrobacterium* cells was an $OD_{660}$ of 0.5. In most experiments, pluronic F68 was added to the inoculation mixture at a final concentration of 0.01%. The ratio between the *Agrobacterium* and immature embryos (IEs) was about 10 mL: 20–200 IEs. The conditions for inoculation were temperatures from about 23° C.–26° C. with a duration from about 5–60 minutes.

Modification of *Agrobacterium* Preparation Method

In the experiment to determine the effect of modifications to the medium and method on the growth of the *Agrobacterium* prior to transformation, *Agrobacterium* was grown on solid medium at 28° C. for 3 days and then at 23° C. for 1 day. The *Agrobacterium* was then directly collected on the solid medium, diluted with ⅒ Cm4C medium and used for inoculation.

The results from 5 experiments (Table 5) showed that the modified method for preparing *Agrobacterium* increased the transformation efficiency. This method also simplified the culture system, saved labor and materials, and reduced cost. Increased flexibility of inoculation time was also an improvement of this change.

[t6]

TABLE 5

Improvement of Agrobacterium preparation method

| Exp. | Treatments | Embryo # | Events | Efficiency % |
|---|---|---|---|---|
| 1 | Control | 450 | 17 | 3.7 |
| 1 | Solid media | 200 | 13 | 6.5 |
| 2 | Control | 180 | 6 | 3.3 |
| 2 | Solid media | 180 | 14 | 7.7 |
| 3 | Control | 300 | 26 | 6.6 |
| 3 | Solid media | 300 | 42 | 1.4 |
| 4 | Control | 330 | 18 | 5.4 |
| 4 | Solid media | 320 | 21 | 6.5 |
| 5 | Control | 340 | 14 | 4.1 |
| 5 | Solid media | 340 | 19 | 5.5 |
| Total | Control | 1600 | 81 | 5 |
|  | Solid media | 1340 | 109 | 8.1 |

Example 6

Culture Temperature

The culture temperature in these experiments includes the culture stages such as preculture, co-culture, delay and selection. Three different temperature treatments were tested, and the data shown here was combined from three replicated experiments. The results illustrate that transformation efficiency peaks at a temperature of 25° C. when compared to 22° C. and 28° C. Thus by culturing at 25° C. throughout the stages of the method, this treatment is about 3 times more efficient than either 22° C. or 28° C., standard temperature variations in such experiments (Table 6).

[t7]

TABLE 6

Effects of culture temperature

| Exp | Treatments | Embryo # | Events | Efficiency % |
|---|---|---|---|---|
| 1 | 22° C. | 200 | 4 | 2 |
| 1 | 25° C. | 200 | 15 | 7.5 |
| 1 | 28° C. | 200 | 6 | 3 |
| 2 | 22° C. | 200 | 6 | 3 |
| 2 | 25° C. | 200 | 12 | 6 |
| 2 | 28° C. | 200 | 5 | 2.5 |
| 3 | 25° C. | 220 | 23 | 10.45 |
| 3 | 28° C. | 220 | 14 | 6.3 |
| Total | 22° C. | 400 | 10 | 2.5 |
|  | 25° C. | 620 | 50 | 8.1 |
|  | 28° C. | 620 | 25 | 4 |

Example 7

Co-Culture

After the inoculation period, the remaining *Agrobacterium* cells were removed from the explants by using the in-house vacuum equipment. A piece of sterile Whatman No. 1 filter paper (to fit the size of the petri plate) was placed in each of 60×15 or 60×20 mm petri dishes without additional liquid or agar-supplemented media. Two hundred microliters of sterile water was placed in the middle of the filter paper. After 2–3 minutes, the inoculated immature embryos were placed in the plates. Usually, 20–50 explants are grouped as one stack (about 1 cm in size and 60–80 mg/stack), with 4–5 stacks on each plate. The plates were immediately parafilmed and then co-cultivated in the dark at 24° C.–26° C. for 2–3 days.

Example 8

Selection and Plant Regeneration

After a 3-day co-cultivation, the *Agrobacterium*-infected precultured immature embryos (PCIE) and embryogenic calli were transferred to CM4C medium (Table 2) supplemented with 500 mg/L carbenicillin and cultured for about seven days. This "delay" medium could also contain glyphosate as discussed in Example 4. The PCIE explants formed embryogenic callus on this medium.

The explants were then transferred to CM4C selection medium with 2 mM glyphosate and 500 mg/L carbenicillin for one week in the dark. All the calli were transferred to MMS0.2C (Table 2) supplemented with 0.1 mM glyphosate and 250 mg/L carbenicillin (first regeneration medium) for an additional two weeks of selection with lighting conditions of about 80 µE. Green spots or shoots formed at the end of this culture period. All the embryogenic calli were transferred to the second regeneration medium MMS0C (Table 2) supplemented with 500 mg/L carbenicillin and 0.02 mM glyphosate. Aromatic amino acids including l-tryptophan, L-tyrosine, and l-phenylalanine ($10^{-7}$ mM/amino acid) were added to this medium to facilitate the selection. These tissues were transferred to fresh media every two weeks. Plantlets with elongated meristems and roots could be regenerated from embryogenic callus tissue any time during the culture period. Once the root system was established, the plants were transferred to soil and subsequently assayed. All the plants originating from the same PCIE or callus were considered as siblings from the same transgenic event.

Example 9

Glyphosate Selection Time Length with CM4C+2 mM Glyphosate

The time in selection media containing glyphosate was extended from 7 days to 10 days. This treatment not only increased the selection stringency but also made transfer time more flexible. The results in Table 7 indicate that 10-day selection in CM4C+2 mM glyphosate medium is more efficient than 7-day selection.

[t8]

TABLE 7

Effects of extending selection period from 7 days to 10 days in CM4C + 2 mM glyphosate medium

| Exp | Treatments | Embryo # | Events | TE % |
|---|---|---|---|---|
| 1 | 7 days | 150 | 6 | 4 |
| 1 | 10 days | 150 | 11 | 7.3 |
| 2 | 7 days | 225 | 5 | 2.2 |
| 2 | 10 days | 225 | 12 | 5.3 |
| 3 | 7 days | 190 | 10 | 5.2 |
| 3 | 10 days | 150 | 13 | 8.6 |
| 4 | 7 days | 400 | 6 | 1.5 |
| 4 | 10 days | 400 | 5 | 1.25 |
| 5 | 7 days | 250 | 11 | 4.4 |
| 5 | 10 days | 250 | 16 | 6.4 |
| Total | 7 days | 1215 | 38 | 3.1 |
|  | 10 days | 1175 | 57 | 4.8 |

Example 10

Increase of Glyphosate Concentration in MMS0.2C Regeneration Medium

The glyphosate concentration in the first regeneration medium was 0.1 mM. By increasing glyphosate concentration to 0.5 mM and 1.0 mM, transformation efficiency was increased (Table 8).

[t9]

TABLE 8

Effects of increasing glyphosate concentration during regeneration stage

| Exp | Treatments | Embryo # | Events | Efficiency % |
|---|---|---|---|---|
| 1 | 0.1 mM gly | 170 | 0 | 0.0 |
| 1 | 0.5 mM gly | 200 | 6 | 3.0 |
| 1 | 1.0 mM gly | 200 | 5 | 2.5 |
| 2 | 0.1 mM gly | 175 | 5 | 2.9 |
| 2 | 0.5 mM gly | 200 | 3 | 1.5 |
| 2 | 1.0 mM gly | 200 | 10 | 5.0 |
| 3 | 0.1 mM gly | 190 | 9 | 4.7 |
| 3 | 0.5 mM gly | 190 | 15 | 7.9 |
| 3 | 1.0 mM gly | 190 | 10 | 5.3 |
| 4 | 0.1 mM gly | 250 | 4 | 1.6 |
| 4 | 0.5 mM gly | 250 | 7 | 2.8 |
| Total | 0.1 mM gly | 785 | 18 | 2.3 |
|  | 0.5 mM gly | 840 | 31 | 3.7 |
|  | 1.0 mM gly | 590 | 25 | 4.2 |

Example 11

Use of Aromatic Amino Acids at Earlier Stages of Wheat Selection and Regeneration The data from five experiments show that AAA applied at selection (CM4C; 7d) and 1st regeneration (MMS0.2C; 14d), in addition to the original protocol at 2nd generation stage (MMS0C; 14d), improved wheat transformation efficiency (TE) 1.8 times. When added at only one stage (MMS0.2C) before the regular MMS0C the effect of AAA on TE was less pronounced (% TE are 2.2 for control and 3.6 for treated, based on data from two independent experiments) than if added during two stages (CM4C and MMS0.2C) earlier before MMS0C (% TE were 4.3 for control and 7.7 for treated, based on data from five independent experiments).

Because increasing glyphosate concentration in MMS0.2C medium improved the transformation efficiency as shown in Table 8, and adding three aromatic amino acids also improved transformation efficiency as shown in Table 9a, two experiments were conducted to find out the best combinations. The results are shown in Table 9b. Transformation efficiencies in treatments 2, 3 and 4 are significantly higher than in treatment 1. These results reconfirmed the effects of increased glyphosate concentration and addition of AAA.

[t10]

TABLE 9a

Aromatic amino acids (AAA) at 0.1 µM present in CM4C media at selection, and in MMS0 2C media at 1st regeneration stages increased transformation efficiency almost twofold

| Exp | Treatments | Embryo # | Events | Efficiency % |
|---|---|---|---|---|
| 1 | CM4C/MMS0.2C | 208 | 5 | 2.4 |
| 1 | CM4C/MMS0.2C + AAA | 208 | 8 | 3.9 |
| 1 | CM4C + AAA/MMS0.2C + AAA | 252 | 17 | 6.8 |
| 2 | CM4C/MMS0.2C | 200 | 5 | 2.5 |
| 2 | CM4C + AAA/MMS0.2C + AAA | 360 | 27 | 7.2 |
| 3 | CM4C/MMS0.2C | 290 | 17 | 5.9 |
| 3 | CM4C + AAA/MMS0.2C + AAA | 290 | 21 | 7.2 |
| Total | CM4C/MMS0.2C | 698 | 27 | 3.9 |
|  | CM4C/MMS0.2C + AAA | 208 | 8 | 3.9 |
|  | CM4C + AAA/MMS0.2C + AAA | 902 | 65 | 7.2 |

* AAA were also present in MMS0C media at 2nd regeneration stage

[t11]

TABLE 9b

Effects of increased glyphosate concentration and addition of AAA in MMS0.2C medium

| | Treatments | Embryo # | Events | Efficiency % |
|---|---|---|---|---|
| 1 | MMS0.2C + 0.1 Gly | 168 | 15 | 8.9 |
| 2 | MMS0.2C + 0.5 Gly | 168 | 23 | 13.7 |
| 3 | MMS0.2C + 0.1 Gly + AAA | 162 | 22 | 13.1 |
| 4 | MMS0.2C + 0.5 Gly + AAA | 162 | 22 | 13.2 |
| 1 | MMS0.2C + 0.1 Gly | 168 | 8 | 4.8 |
| 2 | MMS0.2C + 0.5 Gly | 168 | 13 | 7.7 |
| 3 | MMS0.2C + 0.1 Gly + AAA | 200 | 14 | 7.0 |
| 4 | MMS0.2C + 0.5 Gly + AAA | 190 | 15 | 7.9 |
| Total 1 | MMS0.2C + 0.1 Gly | 336 | 23 | 6.8 |
| 2 | MMS0.2C + 0.5 Gly | 336 | 36 | 10.7 |
| 3 | MMS0.2C + 0.1 Gly + AAA | 362 | 36 | 9.9 |
| 4 | MMS0.2C + 0.5 Gly + AAA | 352 | 37 | 10.5 |

Example 12

Effect of Copper (CuSO$_4$) on Wheat Transformation

One aspect of the invention comprises the use of copper (CuSO$_4$) at a concentration of 2 µM for the initial 14 days of the last stage (MMS0C) of wheat regeneration. In twelve independent experiments, transformation efficiency (TE) of plants regenerated from wheat immature embryos was doubled. TE was consistently higher in Cu-treated callus cultures (16.6% on average in twelve experiments) rather than in control Cu-untreated ones (8.4% on average in twelve experiments), and exceeded controls from 1.3 to 4 times (see Table 1).

[t12]

TABLE 10

Transformation efficiency in control vs CuSO$_4$ treated wheat cultures

| n/n | Exp., # | Control IE, # | Control TE, % | CuSO$_4$, 2 weeks IE, # | CuSO$_4$, 2 weeks TE, % | Cu Trt/Control Ratio, TE |
|---|---|---|---|---|---|---|
| 1 | 1610 | 284 | 8.8 | 200 | 14 | 1.6 |
| 2 | 1616 | 388 | 13.4 | 200 | 17 | 1.3 |
| 3 | 1620 | 252 | 2 | 200 | 7.5 | 3.8 |
| 4 | 1630 | 368 | 33 | 200 | 57 | 1.7 |
| 5 | 1638 | 200 | 3.5 | 200 | 14 | 4 |
| 6 | 1640 | 381 | 20 | 80 | 43.8 | 2.2 |
| 7 | 1689 | 220 | 0.9 | 220 | 3.6 | 4 |
| 8 | 1690 | 300 | 4.3 | 300 | 9 | 2.1 |
| 9 | 1701 | 270 | 6.2 | 260 | 9.2 | 1.5 |
| 10 | 130 | 98 | 1.0 | 109 | 3.7 | 3.7 |
| 11 | 131 | 226 | 5.3 | 72 | 11.1 | 2.1 |
| 12 | 141 | 108 | 2.8 | 107 | 9.3 | 3.3 |
| | Total | 3095 | 8.4 | 2148 | 16.6 | 2.0 |

Preliminary data on cp4 expression by ELISA test confirmed that there were no escapes in glyphosate-selected Cu-treated plants, and that the cp4 gene was expressed at sufficient levels. R0 plants treated with Cu survived commercial levels (64 oz/acre) of glyphosate spray and were advanced to R1 generation.

R1 progeny from thirteen independent R0 lines produced using 2 µM copper, as above, were screened by fluorescence microscopy for the inheritance of the green fluorescent protein gene (gfp). Table 11 demonstrates transmission of gfp to offspring, proving stable germline transformation occurred. The data show that for seven lines, gfp was present in approximately a 3:1 ratio (determined by Chi-Squared analysis), consistent with inheritance of a single locus.

[t13]

TABLE 11

Inheritance of gfp in R1 progeny of copper-treated wheat cultures

| Independent lines | gfp positive | gfp negative | 3:1 Ratio |
|---|---|---|---|
| TA_S16892 | 43 | 0 | No |
| TA_S16898 | 43 | 0 | No |
| TA_S16900 | 30 | 14 | Yes |
| TA_S16901 | 28 | 16 | Yes |
| TA_S16902 | 39 | 5 | No |
| TA_S16906 | 34 | 9 | Yes |
| TA_S16907 | 39 | 3 | No |
| TA_S16908 | 34 | 10 | Yes |
| TA_S16275 | 32 | 11 | Yes |
| TA_S16282 | 39 | 5 | No |
| TA_S16283 | 32 | 11 | Yes |
| TA_S16286 | 29 | 15 | Yes |
| TA_S16284 | 21 | 1 | No |

Experiments were done to confirm that 2 µM CuSO$_4$ improves regeneration in the absence of glyphosate in the media. Five treatments were done: 1) control (0.1 µM Cu as in MS medium) without additional copper; 2) 2 µM copper, applied at delay and selection for 2 weeks total; 3) 2 µM Cu at 1$^{st}$ regeneration for 2 weeks; 4) 2 µM Cu at 2$^{nd}$ regeneration for 2 or more weeks; and 5) 2 µM Cu constantly present at all of these stages.

No improvement occurred in samples where Cu was present at all stages as shown in Table 12. Copper had very little or no effect when applied at the 1$^{st}$ regeneration stage. Some improvement was noticeable when Cu was applied at delay and selection stage. But the most significant increase in regeneration was achieved in the case where Cu was applied at the 2$^{nd}$ regeneration stage of the protocol.

The general number of regenerated shoots was improved (compare 43.5 in control to 80.5 in the treatment) as well as the percentage of regenerable calli (compare 62% in control and 80% in treated). Moreover, the number of shoots per each regenerable callus increased considerably (compare this ratio as 1.4 in control and 2 in Cu-treated when 2 µM copper was applied at 2$^{nd}$ regeneration stage (MMS0C)).

[t14]

TABLE 12

Addition of 2 µM CuSO$_4$ at 2$^{nd}$ regeneration stage increases total no. of shoots, no of regenerable calli, and no of shoots per regenerable callus

| | 0.1 µM Cu Control | 2 µM Cu Delay/Sel. 2 w. | 2 µM Cu 1$^{st}$ Reg. 2 w. | 2 µM Cu 2$^{nd}$ Reg. 2 w. | 2 µM Cu All above 6 w. |
|---|---|---|---|---|---|
| Shoots, # | 43.5 | 57.5 | 44 | 80.5 | 37 |
| Regenerable callus, # | 30.8 | 35.6 | 30.5 | 40 | 30.5 |
| Regenerable callus, % | 62 | 71 | 61 | 80 | 61 |
| Shoots/Regenerable callus, ratio | 1.4 | 1.6 | 1.4 | 2 | 1.2 |
| 1 shoot/callus | 13.5 | 14.3 | 11.8 | 10.8 | 9 |
| 2 shoots/callus | 9.3 | 8.5 | 9.3 | 12.5 | 11.5 |
| 3 shoots/callus | 4.5 | 7.8 | 3.3 | 9.8 | 2.5 |
| 4 shoots/callus | 1 | 0.5 | 1.3 | 4.3 | 0.5 |

* These data are from two experiments

Experiments were also done to compare 0 and 20 µM concentrations of copper in the second regeneration stage (MMSOC media). Results are presented in Table 13.

TABLE 13

Transformation efficiency in control 0 μM & 20 μM
copper-sulfate treated wheat cultures

| Expt # | Explant # | | Independent Events | | % TE | |
|---|---|---|---|---|---|---|
| Copper (μM) | 0 | 20 | 0 | 20 | 0 | 20 |
| 137 | 113 | 50 | 4 | 9 | 3.5 | 18.0 |
| 143 | 62 | 75 | 1 | 6 | 1.6 | 8.0 |
| 149 | 97 | 97 | 0 | 4 | 0 | 4.1 |
| 152 | 145 | 145 | 15 | 26 | 10.3 | 17.9 |
| 161 | 156 | 154 | 12 | 31 | 7.7 | 20.0 |
| Totals | 573 | 521 | 32 | 76 | 5.6 | 14.6 |

The results in Table 13 indicated that addition of 20 μM $CuSO_4$ was a further improvement, with an average copper-treated/control ratio of 2.6, and for individual experiments ratios ranged from 1.7 to as much as 5.1. This apparent improvement was tested in further experiments comparing 0, 2 and 20 μM concentrations of copper in the second regeneration stage (MMSOC media). Results are presented in Table 14.

TABLE 14

Transformation efficiency in control, 2 & 20 μM
copper-sulfate treated wheat cultures

| | Explant # | | | Independent events | | | % TE | | |
|---|---|---|---|---|---|---|---|---|---|
| | | | | Cu (μM) | | | | | |
| Expt # | 0 | 2 | 20 | 0 | 2 | 20 | 0 | 2 | 20 |
| 164 | 126 | 126 | 128 | 7 | 19 | 26 | 5.6 | 15.1 | 20.3 |
| 166 | 242 | 244 | 246 | 22 | 23 | 39 | 9.1 | 9.4 | 15.9 |
| Total | 368 | 370 | 374 | 29 | 42 | 65 | 7.9 | 11.4 | 17.4 |

These results in Table 13 are consistent with the conclusion that 20 μM copper sulfate is a further improvement. Experiments were then done to determine the optimal concentration, and the upper limit of the range over which copper sulfate addition to the second regeneration stage (MMSOC media) was effective. Initially concentrations up to 80 μM were considered, the results of these experiments are presented in Table 15.

TABLE 15

Transformation efficiency in control, 20, 40 & 80 μM
copper-sulfate treated wheat cultures

| Expt # | 292 | 293 | 295 | 296 | 297 | 301 | Total explants | Total Ind. Events | Over all % TE |
|---|---|---|---|---|---|---|---|---|---|
| $CuSO_4$ (μM) | | | % TE | | | | | | |
| 0 | 2.0 | 4.6 | 3.3 | 5.9 | 9.9 | 7.8 | 585 | 32 | 5.5 |
| 20 | 15.0 | 9.3 | 13.0 | 29.7 | 17.3 | 21.4 | 585 | 103 | 17.6 |
| 40 | 14.0 | 13.9 | 22.6 | 21.8 | 20.7 | 19.6 | 586 | 109 | 18.6 |
| 80 | 14.0 | 12.0 | 18.1 | 14.9 | 15.5 | 29.4 | 589 | 98 | 16.6 |

Table 15 results again confirm the efficacy of adding copper sulfate in terms of increasing TE, also they suggest that from 20 to 80 μM inclusive, there is no difference in the magnitude of the response, which averages 17.6%, compared to 5.5% in the control. The next experiment increased the range under study up to a maximum of 3000 μM copper sulfate additions to the second regeneration stage (MMSOC media), results are presented in Table 16.

TABLE 16

Transformation efficiency in control, 40, 250, 500, 750, 1000,
1500, 2000 & 3000 μM copper-sulfate treated wheat cultures

| $CuSO_4$ (μM) | Explants | Transgenics | % TE |
|---|---|---|---|
| 0 | 80 | 2 | 2.5 |
| 40 | 80 | 14 | 17.5 |
| 250 | 80 | 16 | 20.0 |
| 500 | 80 | 19 | 23.75 |
| 750 | 80 | 12 | 15.0 |
| 1000 | 80 | 8 | 10.0 |
| 1500 | 80 | 11 | 13.8 |
| 2000 | 36 | 4 | 11.1 |
| 3000 | 36 | 2 | 5.6 |

Table 16 demonstrates that highly significant improvements in TE are achievable even at concentrations as high as 3000 μM, which with a TE of 5.6% was more than double the control TE of 2.5%. The optimal concentration would appear to lie at approximately 250–500 μM, where TEs of 20 and 24% respectively, represent an order of magnitude in improvement over the control (2.5%).

A study was undertaken to estimate the minimum amount of copper sulfate required to elicit a positive response in TE. Two experiments were set up where 0, 0.25 μM, 0.5 μM, 1.0 μand 2.0 μM additions of copper sulfate were made to the second regeneration stage (MMSOC media); results are presented in Table 17.

TABLE 17

Transformation efficiency in control, 0.25, 0.50, 1.0
and 2.0 μM copper-sulfate treated wheat cultures

| | Explant # | | Transgenic # | | |
|---|---|---|---|---|---|
| $CuSO_4$(μM) | Expt. 309 | Expt. 314 | Expt. 309 | Expt. 314 | % TE |
| 0 | 100 | 108 | 4 | 3 | 3.4 |
| 0.25 | 100 | 108 | 3 | 7 | 4.8 |

TABLE 17-continued

Transformation efficiency in control, 0.25, 0.50, 1.0
and 2.0 μM copper-sulfate treated wheat cultures

|  | Explant # | | Transgenic # | | |
|---|---|---|---|---|---|
| CuSO$_4$(μM) | Expt. 309 | Expt. 314 | Expt. 309 | Expt. 314 | % TE |
| 0.5 | 100 | 108 | 4 | 5 | 4.3 |
| 1.0 | 100 | 108 | 10 | 11 | 10.1 |
| 2.0 | 100 | 108 | 14 | 29 | 20.7 |

Table 17 shows that in experiment 309 no improvement was seen in TE until copper was present at greater than 0.5 μM, whereas in experiment 314 there was a response in the lowest concentration tested (0.25 μM). Therefore an improvement in TE at concentrations of 0.5 μM or less can occur, but not as consistently as responses to larger doses, where improvements in TE were large for both experiments. In general experiment 314 responded better to copper; the improvement in TE for the 1.0 μM treatment was 2.5× for experiment 309, and almost 4× for experiment 314, while at 2.0 μM the response was 3.5× for experiment 309, and almost 10× for experiment 314.

Example 13

Selection with nptII

For nptII selection, immature embryos were isolated, precultured, inoculated, and co-cultured as previously described. After the 3-day co-culture, embryos were transferred to delay culture (solid CM4C2D) media (CM4C media as in Table 2 with 2 mg/L 2,4-D) with 500 mg/L carbenicillin for 7 days in the dark at 25° C. Selection was done in liquid CM4C media (as in Table 2 without the Phytagel) with 100 mg/L carbenicillin and 20 mg/L G418 on a support for 7 days in the dark followed by 7 days in the light (16 hr photoperiod), at 25° C. The calli were then transferred to liquid MMSO0.2C media (as in Table 2 without the gelling agent) with 100 mg/L carbenicillin and 25 mg/L G418 on a support for 2 weeks at 25° C. with a 16 hr photoperiod. After 2 weeks, the calli were transferred to liquid MMSOC media (as in Table 2 without the gelling agent) with 100 mg/L carbenicillin and 25 mg/L G418 on a support for 2 to 4 weeks at 25° C. with a 16 hr photoperiod. Plantlets were transferred to solid MMSOC media with 100 mg/L carbenicillin and 25 mg/L G418 in sundae cups for 1 to 4 weeks at 25° C. with a 16 hr photoperiod.

Copper was also tested in this selection system at 0, 2, and 20 μM in the MMSOC media. Across six different experiments, transformation efficiency at 0 μM copper was 1.2%, at 2 μM copper was 4.5%, and at 20 μM copper was 7.2%, thus demonstrating that copper sulfate can effect large improvements in TE in the nptII system also. See Table 18.

TABLE 18

Transformation efficiency in control, 2 & 20 μM
copper-sulfate treated wheat cultures grown in the
nptII liquid system using two different constructs

| | Transgenics | | | explants | | | % TE | | |
|---|---|---|---|---|---|---|---|---|---|
| | Copper sulfate (μM) | | | | | | | | |
| Expt | 0 | 2 | 20 | 0 | 2 | 20 | 0 | 2 | 20 |
| 169 | 4 | 3 | n/a | 192 | 192 | 0 | 2.08 | 1.56 | n/a |
| 170 | 0 | 8 | n/a | 215 | 215 | 0 | 0.00 | 3.72 | n/a |
| 184 | 2 | 4 | 6 | 185 | 185 | 180 | 1.08 | 2.16 | 3.33 |
| 186 | 1 | 1 | 4 | 175 | 175 | 176 | 0.57 | 0.57 | 2.27 |
| 173 | 6 | 20 | 18 | 191 | 212 | 209 | 3.14 | 9.43 | 8.61 |
| 174 | 1 | 16 | 27 | 175 | 175 | 198 | 0.57 | 9.14 | 13.64 |
| Totals | 14 | 52 | 55 | 1133 | 1154 | 763 | 1.24 | 4.51 | 7.21 |

Example 14

Effect of Other Copper Compounds, and Other Transition Metals on Transformation

Some alternative copper compounds, and some alternative transition metals were tested to determine if these could enhance TE. Alternative copper II salts were tested (chloride, nitrate and acetate), zinc sulfate, cobalt chloride, chelated iron, manganese sulfate and magnesium chloride. All compounds were tested at 20 μM, and some at both 2 and 20 μM. All were tested alongside negative (0 μM copper sulfate) and positive (20 μM copper sulfate) controls, with the exception of Fe-EDDHA which was only compared to a negative control. Two of the metals tested are already present in the MS salts in the basal medium (MMSOC) at a concentration of 100 mM (manganese sulfate and FE-NaEDTA, and magnesium sulfate is at 150 mM. Zinc sulfate is in the MS salts in the basal medium (MMSOC) at close to 30 μM, and this compound was tested at 2 and 20 μM respectively. As in previous experiments, treatments were applied to the second regeneration stage (MMSOC media).

TABLE 19

Transformation efficiency in control, 2 & 20 μM
copper-sulfate treated wheat cultures grown
in the nptII liquid system.

| | | Independent transgenic events/explants % TE | | | |
|---|---|---|---|---|---|
| Compound name/ conc | Expt # | Test compound | 0 μM CuSO$_4$ | 20 μM CuSO$_4$ | 2 μM CuSO$_4$ |
| Copper chloride 2 μM | 236, 243 | 37/220 16.8 | 15/228 6.6 | N/a | 37/220 16.8 |
| Zinc sulfate 2 μM | | 12/219 5.5 | | | |
| Copper chloride 20 μM | 232, 315 | 55/227 24.2 | 29/228 12.7 | 63/228 27.6 | N/a |
| Zinc sulfate 20 μM | 232 | 17/107 15.9 | 21/108 19.4 | 33/108 30.6 | N/a |
| Cobalt chloride 20 μM | 260, 315 | 19/207 9.2 | 13/213 6.1 | 48/211 22.7 | N/a |
| Copper acetate 20 μM | 285, 307 308 | 53/230 23.0 | 23/232 9.9 | 46/275 16.7 | N/a |
| Copper nitrate 20 μM | | 44/255 17.3 | | | |

TABLE 19-continued

Transformation efficiency in control, 2 & 20 μM copper-sulfate treated wheat cultures grown in the nptII liquid system.

| Compound name/conc | Expt # | Test compound | Independent transgenic events/explants % TE | | |
|---|---|---|---|---|---|
| | | | 0 μM CuSO$_4$ | 20 μM CuSO$_4$ | 2 μM CuSO$_4$ |
| Magnesium chloride 20 μM | 286, 287 | 7/231 3.0 | 9/222 4.1 | 53/225 23.6 | N/a |
| Manganese sulfate 20 μM | | 8/189 4.2 | | | |
| Fe-EDDHA 20 μM | 267 | 8/191 4.2 | 13/190 6.8 | N/a | N/a |

The results presented in Table 19 show that 4 compounds either gave no response, or they had a TE equal to, or close to the negative control, and these are all the same compounds as mentioned previously as already present in the basal medium. The compounds were zinc sulfate (at both 2 and 20 μM), magnesium chloride (20 μM), manganese sulfate (20 μM) and Fe-EDDHA (20 μM).

All of the copper compounds tested were extremely effective; they all had much larger TEs than their negative controls. Copper chloride is equally as effective at increasing TE as the copper sulfate positive control in the 2 μM comparison (both 16.8%), and only slightly less effective in the 20 μM comparison (24.2% vs. 27.6%). Copper acetate (23.0%) and copper nitrate (17.3%) both were more effective than the 20 μM copper sulfate positive control (16.7%).

Cobalt chloride at a concentration of 20 μM had a larger TE than the negative control (9.2% vs. 6.1%), showing it is effective at increasing TE, however it was not as effective as 20 μM copper sulfate (22.7%).

The conclusion is that all copper compounds tested were as effective, or more effective than copper sulfate was at an equivalent concentration. Cobalt chloride was more effective than the negative control. All other compounds (i.e., zinc sulfate, magnesium chloride, manganese sulfate, and Fe-EDDHA were not effective for the concentrations tested.

Example 15

Transformation Efficiency

All of the previously discussed improvements were combined in an overall improved protocol over the protocol as disclosed in Cheng and Fry (WO 2000/034491). Table 20 shows that the improvements of the present invention increase the transformation efficiency from 3% to 11.8% on average.

[t22]

TABLE 20

Comparison of New Protocol with Previous Protocol

| Constructs | Treatments | Explants | Events | Efficiency (%) |
|---|---|---|---|---|
| 30159 | previous | 170 | 4 | 2.4 |
| | new | 170 | 34 | 20 |
| 42071 | previous | 320 | 13 | 4.1 |
| | new | 440 | 32 | 7.3 |
| 42072 | previous | 250 | 6 | 2.4 |
| | new | 280 | 14 | 5 |

TABLE 20-continued

Comparison of New Protocol with Previous Protocol

| Constructs | Treatments | Explants | Events | Efficiency (%) |
|---|---|---|---|---|
| 42071 | previous | 221 | 6 | 2.3 |
| | new | 365 | 73 | 12.3 |
| 30159 | previous | 333 | 10 | 3 |
| | new | 298 | 30 | 10.1 |
| Total | previous | 1294 | 39 | 3.0 |
| | new | 1553 | 183 | 11.8 |

Example 16

Detection and Analysis of the Transgenic Plants

The regenerated plants showed no visible abnormalities and were fertile. Many transgenic events were produced.

The plants were grown in an environmentally controlled growth chamber with a 16 hour photoperiod at 800 μmolm$^{-}$$_2$s$^{-1}$ provided by high-intensity discharge (HID) Sylvania lights (GTE Products Corp., Manchester, N.H.). The day/night temperatures were 18/16° C. It took about 2 to 3 months from inoculation to transferring most of the plants to soil, and no visible abnormalities were observed. Each plant can be examined by one or more of the following methods:

1) GUS histochemical calorimetric assay (Jefferson, 1987) using different parts of the plants.

2) A leaf bleach assay as described in Cheng et al. (1997).

3) Southern hybridization analysis (Southern, 1975) is also conducted. Genomic DNA is isolated from leaf tissue of test plants using standard methods known to those of skill in the art (see, for example the method described in Roger and Bendich, 1985). Once the DNA is isolated, Southern analyses can be performed using protocols and methods that are known to those of skill in the art.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the invention has been described in detail for the purpose of illustration, it is understood that such detail is solely for that purpose, and variations can be made therein by those skilled in the art without departing from the spirit and scope of the invention which is defined by the following claims.

REFERENCES

The references listed below and all references cited herein are incorporated herein by reference to the extent that they supplement, explain, provide a background for, or teach methodology, techniques, and/or compositions employed herein.

Amrhein et al., *FEBS Letters.* 157: 191–196, 1983.
Bird et al., *Biotech Gen. Engin. Rev.*, 9:207–227, 1991.
Bregitzer et al., *Plant Cell Reports.* 17: 941–945, 1998.
Castillo et al., *Plant Cell Reports.* 17: 902–906, 1998.
Chau et al., *Science,* 244:174–181, 1989.
Cheng et al., *Plant Physiol.,* 115(3): 971–980, 1997.
Chu, *Proc. Symp. Plant Tissue Culture.* Peking: Science Press. Pp. 43–50, 1978.

Dahleen, *Plant Cell, Tissue and Organ Culture.* 43: 267–269, 1995.

Della-Cioppa et al., *Bio/Technology,* 5:579–584, 1987.

Franz et al., Glyphosate: a unique global herbicide. Washington, D.C. 1997.

Gamborg et al., *Exp. Cell Res.,* 50:151, 1968.

Ghaemi et al., *Plant Cell Tiss. Org. Cult.* 36: 355–359, 1994.

Gibson and Shillitoe, *Mol. Biotech.,* 7:125–137, 1997.

Jefferson, *Plant Mol. Biol. Rep.,* 5:387–405, 1987.

Kay et al., *Science,* 236:1299, 1987.

Kim et al., Abstract. P-1021. In Vitro Cell. Dev. Biol.-Plant. 35: 43-A. *Congress On In Vitro Biology,* Jun. 5-9, 1999.

Klee and Rogers, *Cell Culture and Somatic Cell Genetics of Plants.* Academic Press. 6:1–23, 1989.

Knutson et al., *Proc. Natl. Acad. Sci. USA,* 89:2624–2628, 1992.

McCown and Lloyd, *HortScience,* 16:453, 1981.

Miller, Cold Spring Harbor Laboratory Press, Cold Spring Harbor, N.Y., 1972.

Morard et al., *Plant Cell Reports.* 18: 260–265, 1998.

Morillo et al., *Environ. Sci. Technol.* 31: 3588–3592, 1997.

Murashige and Skoog, *Physiol. Plant,* 15:473–497, 1962.

Nitsch and Nitsch, *Science,* 163:85–87, 1969.

Odell et al., *Nature,* 313:810, 1985.

Piorer et al., *Science,* 256:520–523, 1992.

Poszkowski et al., *EMBO J.,* 3:2719, 1989.

Purnhauser, *Cereal Research Communications.* 19: 419–423, 1991.

Purnhauser and Gyulai, *Plant Cell, Tissue and Organ Culture.* 35: 131–139, 1993.

Roger and Bendich, *Plant Mol. Biol.,* 5:69–76, 1985.

Sambrook et al., *Molecular Cloning: A Laboratory Manual,* Second Edition, Cold Spring Harbor Laboratory Press, Cold Spring Harbor, N.Y., 1989.

Schenk and Hildebrandt, *Can. J. Bot.* 50:199–204, 1972.

Shook and Guenzi, *Thesis. Oklahoma State University.* 1996.

Smart et al., *The Journal of Biol. Chem.* 260: 16338–16346, 1985.

Southern, *Mol. Biol.,* 98:503–517, 1975.

Vasil et al., *Bio/Technology,* 10:667–674, 1992.

Vasil et al., *Bio/Technolgy,* 11:1153–1158, 1993.

Weeks et al., *Plant Physiol,* 102:1077–1084, 1993.

Woeste et al., *Physiologia Plantarum.* 105: 478–484, 1999.

The invention claimed is:

1. A method for transforming a corn, rice, barley, or wheat plant using an *Agrobacterium*-mediated process, comprising:
   (a) preculturing at least one immature embryo from a corn, rice, barley, or wheat plant in a first medium containing increased MS salts from between about 1.5 times standard to about 3 times standard and a concentration of picloram from between about 2.5 mg/L to about 5 mg/L for a period of time sufficient to form a precultured embryo;
   (b) contacting the precultured embryo with *Agrobacterium* capable of transferring at least one gene construct thereto;
   (c) co-cultivating the precultured embryo with *Agrobacterium*; and
   (d) regenerating plants expressing the gene construct.

2. The method of claim 1 in which after the co-cultivating, the embryo is cultured in a second medium containing a selective agent to select for embryos expressing a gene construct that confers resistance to the selective agent.

3. The method of claim 1 in which the MS salts are double the standard concentration and the picloram concentration is 4 mg/L.

4. The method of claim 1 in which the plant is wheat.

5. The method of claim 1 in which the plant is rice.

6. The method of claim 1 in which the plant is barley.

7. The method of claim 1 in which the plant is corn.

* * * * *

UNITED STATES PATENT AND TRADEMARK OFFICE
CERTIFICATE OF CORRECTION

PATENT NO.        : 7,238,862 B2                                    Page 1 of 1
APPLICATION NO.   : 10/064849
DATED             : July 3, 2007
INVENTOR(S)       : Allison et al.

It is certified that error appears in the above-identified patent and that said Letters Patent is hereby corrected as shown below:

Title Page, Item (54) Title: please delete "EFFICIENCY" and please insert --EFFICIENT--.

Signed and Sealed this

Eleventh Day of September, 2007

JON W. DUDAS
*Director of the United States Patent and Trademark Office*